(12) United States Patent
Constantino

(10) Patent No.: US 7,131,840 B2
(45) Date of Patent: Nov. 7, 2006

(54) DENTAL IMPLANT INSTALLATION METHOD AND DEVICE

(76) Inventor: Aziz Constantino, Rua Monte Alegre, 173, 05014 Sao Paolo, SP (BR)

( * ) Notice: Subject to any disclaimer, the term of this patent is extended or adjusted under 35 U.S.C. 154(b) by 0 days.

(21) Appl. No.: 10/161,199

(22) Filed: Jun. 3, 2002

(65) Prior Publication Data

US 2003/0224327 A1 Dec. 4, 2003

(51) Int. Cl.
- *A61C 3/00* (2006.01)
- *A61C 8/00* (2006.01)
- *B25B 13/48* (2006.01)

(52) U.S. Cl. .................. 433/141; 433/173; 81/436

(58) Field of Classification Search ......... 433/141 OR, 433/163, 172, 173 X, 174, 175, 176, 29, 433/215; 206/63.5, 368; 81/436 X
See application file for complete search history.

(56) References Cited

U.S. PATENT DOCUMENTS

| | | | |
|---|---|---|---|
| 4,193,194 A | | 3/1980 | Dalise .................... 433/177 |
| 5,061,181 A | * | 10/1991 | Niznick ................... 433/173 |
| 5,105,690 A | * | 4/1992 | Lazzara et al. ............. 81/436 |
| 5,582,299 A | * | 12/1996 | Lazzara et al. ........... 206/63.5 |
| 5,749,732 A | | 5/1998 | Sendax .................... 433/174 |
| 6,464,500 B1 | * | 10/2002 | Popovic .................... 433/173 |

OTHER PUBLICATIONS

Intra-Lock brochure, Apr./ May 2001.*
IMTEC Sendax Mini Dental Implant System (MDI) Small Wonder 4-page color brochure.
Dental Attachment Systems The AIT Attachment for Retained Natural Tooth Roots pp. 6 and 7, Nov. 13, 2001.

* cited by examiner

*Primary Examiner*—John J Wilson
(74) *Attorney, Agent, or Firm*—Reising, Ethington, Barnes, Kisselle, P.C.

(57) ABSTRACT

A dental implant installation method and device for picking up a prosthetic support implant, transporting it to an osteotomy site, then transmitting rotational force from a drill to the implant to thread the implant into bone tissue at the osteotomy site. The device includes an alignment section that aligns and rotationally engages the device in a socket of a threaded implant. An aft end of the device is configured to releasably engage a drill and to transmit turning forces from such drill to the device. A retainer supported on the shaft adjacent the alignment section releasably engages and retains the implant against axial disengagement once the alignment section has been inserted into the socket.

21 Claims, 3 Drawing Sheets

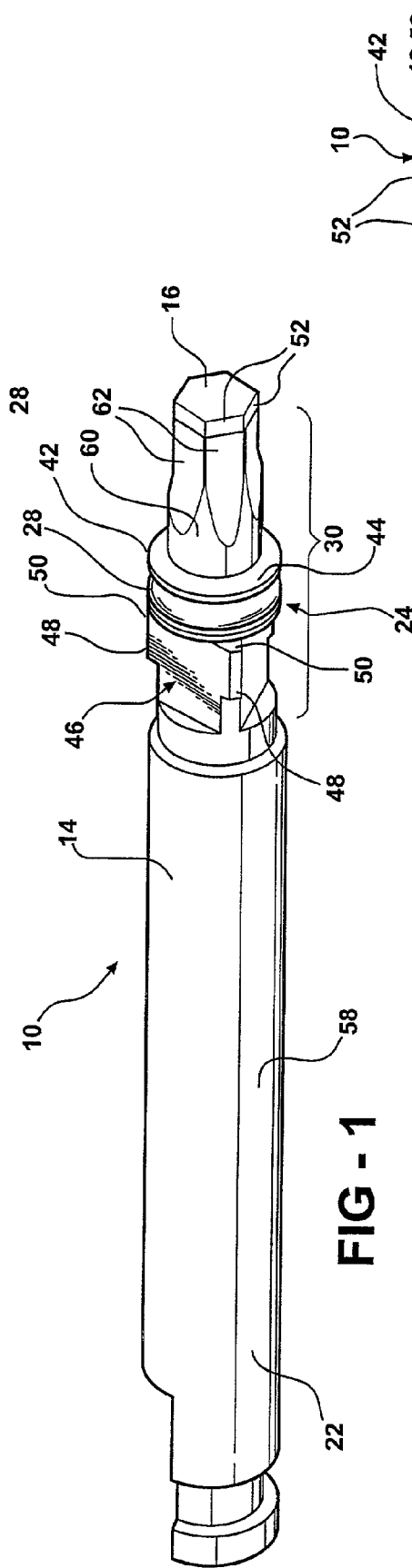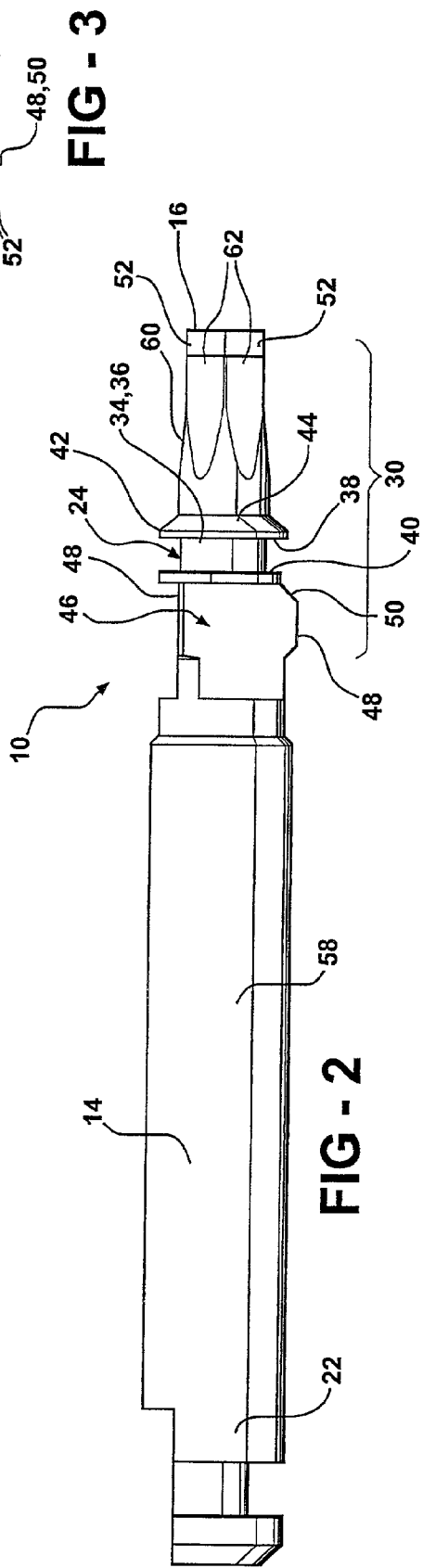

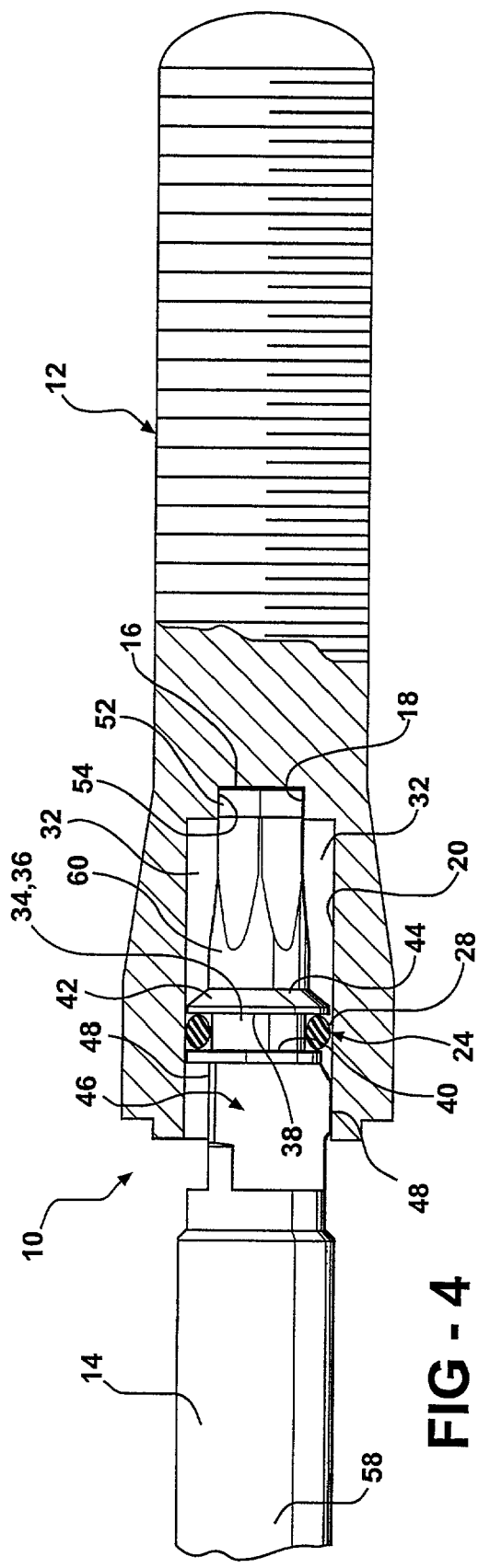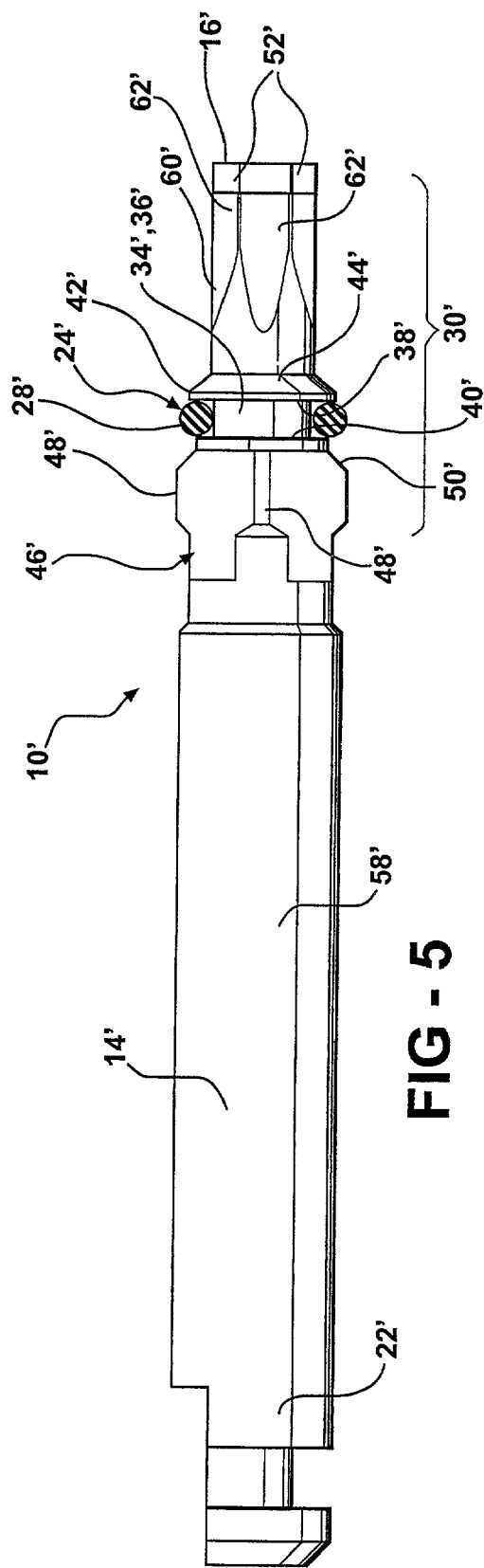

DENTAL IMPLANT INSTALLATION METHOD AND DEVICE

CROSS-REFERENCES TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

This invention relates generally to the installation of dental prosthetic support implants, more specifically, to a method and device for engaging and removing a dental implant from its packaging, then transmitting rotational force from a drill, by hand or with a ratchet to the implant to thread the implant into bone tissue.

2. Description of the Related Art Including Information Disclosed Under 37 CFR 1.97 and 1.98

Dental prosthetic support implants are used to support prosthetic teeth on a patient's jaw bone. They are generally delivered in a sterile condition within a storage vial. To reduce risk of infection, the implants must be removed from the vial and installed in a manner that prevents contamination. Each implant generally includes a threaded shaft that is threaded into a pilot hole (osteotomy site) formed in a jaw bone through an opening formed by cutting and laying back a surgical flap of the gum tissue covering the bone. Once the implant has been installed, either at the time of implantation of at a later time, the gum tissue is closed around the implant with a stem of the implant protruding upward through the gum tissue. Once the gum tissue has healed around the implant, a prosthetic tooth is formed around or mounted on the protruding implant stem. Some implants also include hexagonal sockets formed axially downward into the respective top ends of their stems or hexagonal nuts formed integrally and axially upward from the respective top ends of their stems. The hexagonal configuration of such a socket or nut serves to prevent relative rotation of a prosthetic tooth that has been formed onto the stem and into or onto the socket. The socket or nut may be of any suitable shape, e.g., octagonal, triangular or a spline connection.

It is known to use a dental implant installation device to install an implant of this type by engaging and transmitting rotational force from a drill to the implant. For example, Intra-Lock, the assignee of the present invention, has produced a line of implant installation devices and implants known as the Conic Line Mount System. The Conic Line Mount device includes an elongated shaft and a hexagonal, tapered driver head disposed at a forward end of the shaft. The driver head is shaped to engage an axially internal hexagonal drive socket of a specially-designed dental implant, bypassing the prosthetic interface socket of the implant. The internal drive socket is formed in an axially inner wall of the outer prosthetic interface socket preventing damage to the prosthetic interface socket by providing an alternative driver engagement socket. An aft end of the shaft of the device includes a latch and shank configuration for releasably engaging a drill and transmitting turning forces from such drill to the device. However, the Conic Line Mount driver device can't positively engage and retain implants for transport to an osteotomy site. Implants are supported loosely on the Conic Line Mount driver and, if not supported by other means, can fall off the driver device. Also, torque loading is limited for this system because the tapered head of the Conic Line Mount driver device must engage generally parallel walls of the drive socket. Also, the diameter might not allow the driver to withstand heavy torque in dense bone, and the driver might break. That's why the conic driver has evolved to mimic the hex driver. The conic driver has an identical shape but is homothetically bigger.

U.S. Pat. No. 4,193,194 issued 18 Mar. 1980 to Dalise discloses a dental implant that includes a post having a base engageable within a natural tooth root and an upper end engageable within a generally cylindrical aperture in the base of a dental prosthesis. A circumferential kerf is formed into an outer circumferential surface of the post, and a corresponding kerf is formed in an inner circumferential surface of the aperture in the prosthesis. A resilient ring is received in and around and is retained by the circumferential kerf in the post. The kerf in the prosthesis receives the resilient ring when the denture is forced downward onto the implant post. The ring thus provides circumferential retention of the denture on the implant post.

A more effective implant installation device and method is needed—one that can positively engage, pick up, retain, and transmit rotational force to a prosthetic support implant to thread the implant into bone tissue without compromising sterility. The industry's answer to this need has been the use of an implant mount comprising a metal counterpart that retains an implant by engaging the implant's anti-rotational device (a hex nut, for example). Problems associated with such implant mounts include the cost of fabricating a complex machined part, the need to make it disposable, potential deformation of a prosthetic connection due to the high amount of torque that must be applied to the connection to drive the implant into dense bone, and the time needed to unfasten the mount once the implant has been placed.

BRIEF SUMMARY OF T INVENTION

The invention is a dental implant installation device for engaging and picking up a prosthetic support implant then transmitting rotational force from a drill to the implant to thread the implant into bone tissue. The device includes an elongated shaft, an alignment section carried by the shaft and configured to align and rotationally engage the device in an implant socket An aft end of the shaft is configured to releasably engage a drill and to transmit turning forces from such drill to the device. The dental implant installation device also includes a retainer supported on the shaft adjacent the alignment section and configured to releasably engage and retain the implant against axial disengagement once the alignment section has been inserted into the socket. Therefore, a dental implant installation method and device constructed according to the invention is better able to positively engage and retain an implant for transport from a sterile storage vial to an osteotomy site for installation.

According to another aspect of the invention, the alignment section includes generally radially outwardly extending device detent surfaces positioned to engage and transmit turning forces to generally radially oriented socket detent surfaces formed in an implant socket. By aligning turning force application vectors in respective directions more perpendicular to the detent surfaces, this arrangement prevents stripping and other forms of implant deformation that might otherwise occur under higher torque loads experienced when an implant encounters dense bone tissue.

The invention also includes a method for engaging and picking up a prosthetic support implant then transmitting rotational force from a drill to the implant to thread the implant into bone tissue. According to the method, one can install a prosthetic support implant by providing a threaded implant having an axially oriented socket disposed axially opposite a threaded end of the implant and also providing a dental implant installation device comprising an elongated shaft, an alignment section carried by the shaft and configured to engage and transmit turning forces to the socket of the implant, and a retainer supported on the shaft. Inserting the device into the socket until the retainer engages socket. The implant is then lifted and transported to an osteotomy site by lifting and carrying the installation device with the implant supported on the device. The implant is then inserted and threaded into the pilot hole formed at the osteotomy site by applying torque to the implant installation device. The device is then withdrawn from the implant.

BRIEF DESCRIPTION OF THE SEVERAL VIEWS OF THE DRAWINGS

These and other features and advantages of the invention will become apparent to those skilled in the art in connection with the following detailed description and drawings, in which:

FIG. 1 is an isometric view of a dental implant installation device constructed according to a first embodiment of the invention;

FIG. 2 is a side view of the dental implant installation device of FIG. 1 with an O-ring of the device removed for clarity;

FIG. 3 is a forward end view of the dental implant installation device of FIG. 2;

FIG. 4 is a partial side view of the dental implant installation device of FIG. 1 inserted into a threaded dental implant;

FIG. 5 is a side view of a dental implant installation device constructed according to a second embodiment of the invention.

DETAILED DESCRIPTION OF INVENTION EMBODIMENT(S)

Figure 6:
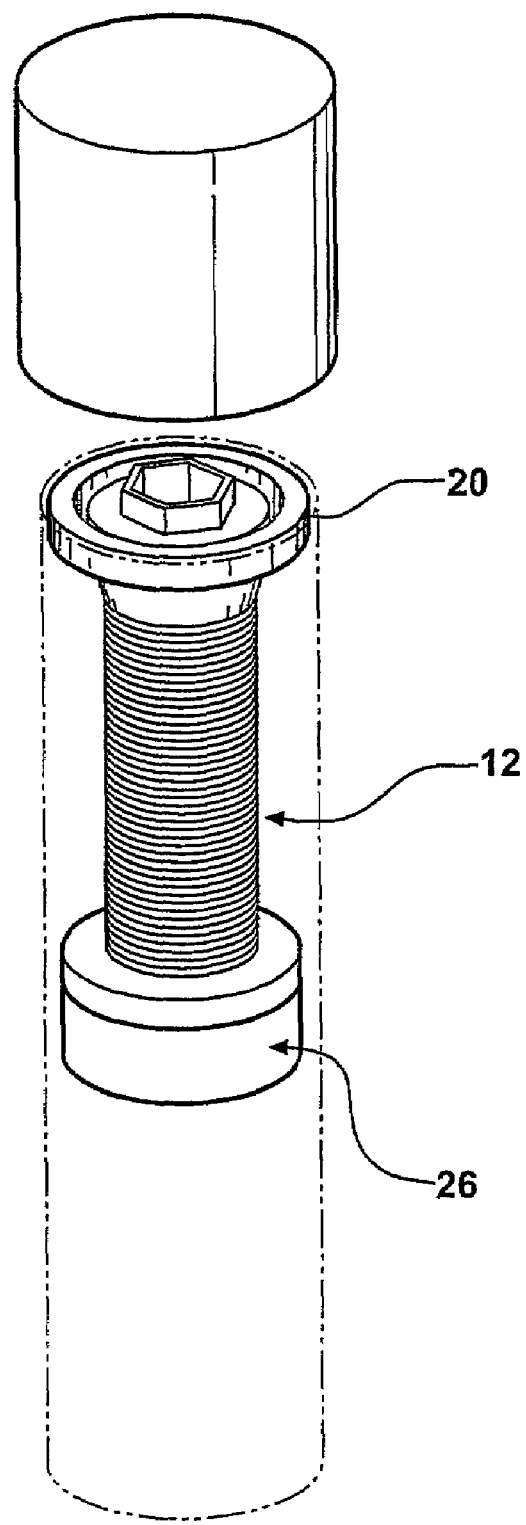
FIG. 6 is an isometric view of a dental implant disposed within a protective vial with its cap removed exposing a socket of the implant.

A first embodiment of a dental implant 12 installation device constructed according to the present invention is generally indicated at 10 in FIGS. 1–4. A second embodiment is generally indicated at 10' in FIG. 5. Reference numerals with the designation prime (') in FIG. 5 indicate alternative configurations of elements that also appear in the first embodiment. Unless indicated otherwise, where a portion of the following description uses a reference numeral to refer to the figures, that portion of the description is intended to apply equally to elements designated by primed numerals in FIGS. 1–4.

The device 10 is designed to engage a prosthetic support implant such as the implant shown at 12 in FIGS. 4 and 6 having an axial socket 20 disposed axially opposite a threaded end of the implant 12. When engaged, the device 10 is capable of transmitting rotational force from a drill to the implant 12 to thread the implant 12 into bone tissue. The device 10 includes an elongated shaft 14 and a driver head 16 disposed at a forward end of the shaft 14. As is best shown in FIG. 4, the driver head 16 is shaped to engage and transmit turning forces to an implant cover screw (not shown), allowing the device 10 to double as a screwdriver for installing cover screws in implants that use such cover screws. An aft end 22 of the shaft 14 releasably engages a drill to transmit turning forces from such drill to the device 10. A retainer 24 supported on the shaft 14 releasably engages and retains an implant 12 against axial disengagement when the device 10 is inserted into the socket 20 of an implant 12.

The retainer 24 provides an interference fit between the device 10 and the socket 20 of an implant 12 sufficient to prevent an implant 12 from falling off the device 10 when the device 10 is being used to retrieve such an implant 12 from a sterile storage vial or the like. A dental implant 12 is shown stored in such a vial 26 in FIG. 6. The retainer 24 also prevents an engaged dental implant 12 from falling off the device 10 as the device 10 is used to carry the implant 12 to an osteotomy site and to insert the implant 12 into a pilot hole formed in the bone at the site. However, the interference fit is not so snug as to prevent the device 10 from being easily removed from an implant 12 once the implant 12 has been fully installed.

The retainer 24 includes a resilient rubber O-ring 28 supported on an insertion portion 30 of the shaft 14 as shown in FIGS. 1 and 4. The O-ring 28 is inserted with the insertion portion 30 of the shaft 14 into the socket 20 of an implant 12. To prevent the O-ring 28 from sliding off during insertion, it's supported against axial motion relative to the shaft 14. As best shown in FIG. 4, the O-ring 28 has an outer diameter that's greater than the diameter of the insertion portion 30 of the shaft 14. As is also best shown in FIG. 4, the O-ring 28's outer diameter is also greater than the smallest diametrical distance measured across and between opposing facets 32 of the socket 20. This is to insure an interference fit sufficient to retain the insert on the installation device 10. In other embodiments, the O-ring might comprise a material other than rubber.

The retainer 24 also includes a circumferential kerf 34 formed around the insertion portion 30 of the shaft 14 to receive and support the O-ring 28 against axial movement relative to the shaft 14. As best shown in FIGS. 2 and 4, the kerf 34 is essentially a circumferential trench formed around the shaft 14 and defined by a cylindrical kerf floor 36 and forward and aft parallel annular sidewalls 38, 40 that extend integrally and radially outward from the kerf floor 36. The diameter of the cylindrical kerf floor 36 approximates the inner diameter of the O-ring 28 so that the O-ring 28 can be mounted around the kerf floor 36. A forward wall 38 of the kerf 34 is defined by a forward annular lip 42 that extends integrally and radially outward from the shaft 14. A leading edge of the forward lip 42 comprises a frusto-conical ramp 44 shaped to help co-axially align the O-ring 28 with the socket 20 during insertion of the device 10. The ramp 44 also eases installation of the O-ring 28 in the kerf 34. The O-ring 28 is installed by pushing it axially over the frusto-conical ramp 44, causing it to distend radially until past the forward lip 42, then to retract radially as it moves into kerf 34.

The aft wall 40 of the kerf 34 is defined by an aft annular lip that extends integrally and radially outward from the shaft 14. The aft wall 40 prevents the O-ring 28 from being forced axially aft along the shaft 14 during insertion.

The aft end 22 of the shaft 14 has a latch and shank configuration adapted to engage a drill chuck. The latch and shank configuration of the aft end 22 of the shaft 14 is shaped according to ISO 1797-1 with edge breaks per AS342, note 3. However, in other embodiments the aft end 22 of the shaft 14 may have any shape necessary to connect to any one of a number of different drills known in the art.

The shaft 14 includes an alignment section 46 disposed adjacent and aft of the kerf 34. The alignment section 46 rotationally aligns the device 10 for rotational engagement with the socket 20. The alignment section includes generally radially outwardly extending device detent surfaces positioned to engage and transmit turning forces to corresponding socket detent surfaces formed in an implant socket. In the present embodiment the socket detent surfaces are in corners formed between facets 32 of the socket 20 of the implant. The socket 20 is hexagonal having six facets disposed so as to form six corners at their interfaces. As such, the alignment section 46 has the general shape of a triangular prism with the device detent surfaces disposed on three apexes 48 of the triangular prism shaped and positioned to engage socket detent surfaces defined by every other corner formed between the six facets 32 of the socket 20. The axially leading edges 50 of the apexes 48 of the triangular prism are beveled to help co-axially align the insertion portion 30 of the shaft 14 and the O-ring 28 with the socket 20 during axial insertion of the device 10.

The driver head 16 is circumferentially faceted, having a hexagonal configuration including six facets 52 arranged to form a hexagonal prism, i.e., a "hex head". The driver head 16 is shaped to positively engage complimentary and generally parallel hexagonally configured facets of a circumferentially faceted screw socket (not shown). Certain implants, such as the one shown at 12 in FIG. 4, may include an inner axial recess 18 shaped to receive the driver head 16 to help maintain the axial alignment of the device 10 within the socket 20.

A main portion 58 of the shaft 14 and an aft end of a driver shaft portion 60 of the shaft 14 each have larger diameters than the driver head 16. The driver shaft portion 60 of the shaft 14 is tapered from the aft end of the shaft 14 to the smaller diameter driver head 16. The tapered portion of the shaft 14 includes facets 62 corresponding to and aligned with the facets 52 of the driver head 16. Unlike the driver head 16 of the first embodiment, the driver head 16' of the second embodiment of the invention shown in FIG. 5 has the same approximate diameter as the aft end of a driver shaft portion 60' of its shaft 14'. In practice, a dental implant 12 can be installed according to the invention by first inserting the alignment section 46 of the device 10 into the socket 20 of an implant 12. Since dental implants 12 are generally shipped and stored in sterile vials 26, the vial 26 containing an implant 12 must first be opened to expose the socket 20 of the implant 12 as shown in FIG. 6. The device 10 is inserted into the socket 20 until the retainer O-ring 28 is compressed between the shaft 14 and the socket 20 as shown in FIG. 4. The implant 12 is then extracted from its vial 26 by pulling axially aft on the device 10 and away from the vial 26 with the implant 12 supported by the retainer O-ring 28 from the insertion portion 30 of the shaft 14. The device 10 can then be used to carry the implant 12 to an osteotomy site without having to touch and contaminate the implant 12. The aft end 22 of the shaft 14 of the device 10 can be connected to a drill either before or after the implant 12 is removed from its protective vial 26. A threaded tip of the implant 12 can then be presented in a pilot hole at the osteotomy site and the drill actuated to screw the implant 12 into the bone.

Should the implant 12 encounter dense bone material during insertion, the broad contact area and more perpendicular relationship between torque vectors and the detent surfaces on the apexes 48 of the alignment section 46 and the corresponding detent surfaces disposed in the corners defined by the parallel hex facets 32 of the socket 20 will prevent the driver head 16 from stripping the socket 20. And, because there is no metal to metal contact between the device 10 and the socket 20, the insertion process cannot damage the socket 20. Once the implant 12 has been fully inserted into the bone, the device 10 can be removed from the implant 12 by simply pulling axially outward on the device 10.

The invention provides an implant installation device design that allows a single device to be used to install a plurality of implants without wearing out. Because the cost of such a device can easily exceed the cost of the implant it is designed to install, the reusability of this design results in a significant cost savings.

This description is intended to illustrate certain embodiments of the invention rather than to limit the invention. Therefore, it uses descriptive rather than limiting words. Obviously, it's possible to modify this invention from what the description teaches. Within the scope of the claims, one may practice the invention other than as described.

What is claimed is:

1. A dental implant installation device for engaging and picking up a prosthetic support implant then transmitting rotational force from a drill to the implant to thread the implant into bone tissue, the device comprising:
    an elongated shaft;
    an alignment section carried by the shaft and configured to align and rotationally engage the device in an implant socket;
    an aft end of the shaft being configured to releasably engage a drill and to transmit turning forces from such drill to the device; and
    a resilient retainer supported on the shaft adjacent the alignment section in a position to releasably engage and retain the implant against axial disengagement once the alignment section of the device has been inserted into the implant socket.

2. A dental implant installation device as defined in claim 1 in which:
    the retainer includes a resilient O-ring;
    the O-ring is supported against axial motion relative to the shaft; and
    the O-ring has an outer diameter slightly greater than an inner diameter of an axially oriented socket of a threaded implant to be engaged.

3. A dental implant installation device as defined in claim 2 in which:
    the shaft includes a circumferential kerf configured to receive and support the O-ring against axial movement relative to the shaft; and
    the inner diameter of the O-ring approximates the diameter of the kerf.

4. A dental implant installation device as defined in claim 2 in which the O-ring comprises rubber.

5. A dental implant installation device as defined in claim 1 in which the alignment section includes generally radially outwardly extending device detent surfaces positioned to engage and transmit turning forces to corresponding detent surfaces formed in an implant socket.

6. A dental implant installation device as defined in claim 5 in which:
    a forward wall of the kerf is defined by an annular lip extending integrally and radially outward from the shaft; and
    a leading edge of the annular lip comprises a frustoconical ramp configured to help coaxially align the O-ring with the socket during insertion of the device.

7. A dental implant installation device as defined in claim 1 in which the aft end of the shaft has a latch and shank configuration.

8. A dental implant installation system comprising:
a threaded implant including a threaded tip and a socket formed in an aft end of the implant opposite the threaded tip;
an implant installation device comprising an elongated shaft, an alignment section carried by the shaft and configured to align and rotationally engage the device in the socket of the threaded implant to transmit turning forces to the implant, an aft end of the shaft being configured to releasably engage a drill and to transmit turning forces from such drill to the device;
a resilient retainer supported on the shaft in a position to releasably retain the implant against axial disengagement once the alignment section of the device has been inserted into the socket of the implant;
the socket of the implant is defined by a plurality of generally radially oriented socket detent surfaces; and
the alignment section of the installation device includes generally radially outwardly extending device detent surfaces positioned to engage the socket detent surfaces of the implant as the installation device is inserted into the implant and to transmit turning forces to the implant.

9. A dental implant installation system as defined in claim 8 in which:
the implant socket is a hexagonal socket;
the alignment section has the general shape of a triangular prism including three apexes; and
the three apexes of the triangular prism are shaped and positioned to engage every other corner formed between six parallel facets of the hexagonal prosthetic engagement socket of the implant as the installation device is inserted into the implant.

10. A dental implant installation system comprising:
a threaded implant including a threaded tip and a socket formed in an aft end of the implant opposite the threaded tip;
an implant installation device comprising an elongated shaft, an alignment section carried by the shaft and configured to align and to rotationally engage and transmit turning forces to the implant, an aft end of the shaft being configured to releasably engage a drill and to transmit turning forces from such drill to the device; and
a retainer comprising a resilient O-ring supported on the shaft in a position where the O-ring is disposed within the socket of the implant and releasably holds the implant on the device when the alignment section is engaged within the socket of the implant.

11. A dental implant installation system as defined in claim 10 in which the retainer provides an interference fit between the device and the socket of an implant.

12. A dental implant installation system as defined in claim 11 in which:
the resilient O-ring is supported on an insertion portion of the shaft that is disposed within the socket of the implant when alignment section is engaged within the socket of the implant;
the O-ring is supported against axial motion relative to the shaft; and
the O-ring has an outer diameter slightly greater than an inner diameter of the socket of the implant.

13. A dental implant installation device as defined in claim 12 in which:
the shaft includes a circumferential kerf configured to receive and support the O-ring against axial movement relative to the shaft;
the inner diameter of the O-ring approximates the diameter of the kerf;
a forward wall of the kerf is defined by an annular lip extending integrally and radially outward from the shaft;
a leading edge of the annular lip comprises a frusto-conical ramp configured to help coaxially align the O-ring with the socket of an implant during insertion of the device; and
the frusto-conical ramp is configured to coaxially align the O-ring with the socket of an implant during insertion of the device into the socket of an implant.

14. A dental implant installation device as defined in claim 13 in which:
the alignment section has the general shape of a triangular prism including three apexes; and
the three apexes of the triangular prism each include a generally radially oriented engagement surface shaped and positioned to engage corresponding engagement surfaces formed in the socket of an implant as the installation device is inserted into the socket of the implant.

15. A method for engaging and picking up a prosthetic support implant then transmitting rotational force from a drill to the implant to thread the implant into bone tissue; the method including the steps of:
providing a threaded implant having an axial socket formed axially opposite a threaded end of the implant;
providing a dental implant installation device comprising an elongated shaft, an alignment section carried by the shaft being configured to engage and transmit turning forces to the socket of the implant;
supporting a resilient retainer on the shaft;
rotating the device until the alignment section is positioned to engage the socket of the implant;
inserting the device into the socket of the implant until the alignment section is engaging the detent surfaces of the socket and the resilient retainer engages the socket of the implant;
lifting and transporting the implant by lifting and carrying the installation device with the implant supported on the device;
threading the implant into bone tissue by applying torque to the implant installation device; and
withdrawing the device from the implant.

16. The method of claim 15 in which the step of providing a threaded implant includes providing the implant in a sealed vial.

17. The method of claim 16 including the additional step of opening the vial to expose the socket of the implant before the step of inserting the device into the socket of the implant.

18. The method of claim 17 in which the step of inserting the device includes supporting the implant for device insertion by holding the vial containing the implant.

19. The method of claim 15 including the additional steps of forming a pilot hole in the bone tissue and inserting a threaded tip of the implant into the pilot hole before the step of threading the implant into the bone tissue.

20. The method of claim 15 in which the step of supporting a retainer on the shaft includes supporting a resilient retainer on the shaft, the retainer being shaped and sized to require compression of at least a portion of the retainer during the step of inserting the device.

21. The method of claim 20 in which the step of inserting the device includes inserting the device until the resilient retainer is compressed between the shaft of the device and an inner wall of the socket of the implant.

* * * * *